United States Patent [19]
Matthews

[11] Patent Number: 4,944,289
[45] Date of Patent: Jul. 31, 1990

[54] METHOD AND APPARATUS FOR HEADACHE RELIEF

[76] Inventor: Charles J. Matthews, Medical Arts Building, Suite 104, 1135 Carthage St., Sanford, N.C. 27330

[21] Appl. No.: 426,118

[22] Filed: Oct. 24, 1989

[51] Int. Cl.[5] .......................... A61H 7/00; A61F 5/08; A61F 5/24; A61F 13/12

[52] U.S. Cl. .................................... 128/60; 128/76 R; 128/97.1; 128/163

[58] Field of Search ................ 128/97.1, 60, 402, 163, 128/DIG. 20, 76 R; 2/171.2, DIG. 11, DIG. 10, 171, 185 R

[56] References Cited

U.S. PATENT DOCUMENTS

| | | | |
|---|---|---|---|
| 1,567,931 | 12/1925 | Epler . | |
| 2,286,525 | 6/1942 | Woodward | 128/97.1 |
| 2,453,934 | 11/1948 | Preston | 128/97.1 |
| 2,825,328 | 3/1958 | Olsen . | |
| 3,159,160 | 12/1964 | Ullom | 128/97.1 |
| 3,687,143 | 8/1972 | Schneeberger | 128/402 |
| 3,820,780 | 6/1974 | Tarbox | 128/97.1 |
| 4,204,543 | 5/1980 | Henderson | 128/402 |
| 4,248,215 | 3/1981 | Bleakley | 128/97.1 |
| 4,411,258 | 10/1983 | Pujals, Jr. | 128/60 |
| 4,646,728 | 3/1987 | Takeda | 128/97.1 |

FOREIGN PATENT DOCUMENTS 0289151 4/1928 United Kingdom .

*Primary Examiner*—Robert A. Hafer
*Assistant Examiner*—Michael Brown
*Attorney, Agent, or Firm*—Robert G. Rosenthal

[57] ABSTRACT

A headache relieving headband is disclosed. The headband includes an annular strip of material having an outwardly presented surface and an inwardly presented surface. A channel is defined by the inwardly presented surface and the outwardly presented surface and extends longitudinally along at least a portion of the annular strip of material. A plurality of pressure inducers are adapted to apply pressure simultaneously to preselected points on the cranium.

15 Claims, 1 Drawing Sheet

METHOD AND APPARATUS FOR HEADACHE RELIEF

FIELD OF THE INVENTION

This invention relates generally to the field of neurology and more particularily to the field of headache treatment.

BACKGROUND OF THE INVENTION

Headache is not a disease, but a symptom. Generally, there are three basic processes underlying headaches: mechanical, toxic and functional. Under the foregoing classifications there are over two hundred separate causes of headaches.

A common mechanical cause of headaches is dialation of the blood vessels of the head by a temporary excessive blood supply under too great a pressure. Another common source of headaches is tenseness in the muscles of the head and neck. This type of headache can be caused by local injury, nervous disturbance or even emotional tension.

Headaches are commonly treated with mild analgesics such as aspirin which is the least injurious to barbituates, which may have toxic side effects. While medication is often effective in treating headaches, it is not without risk due to toxic side effects and/or the possibility of an adverse reaction.

In view of the foregoing, it is an object of the present invention to provide a treatment for certain types of headaches in a non-pharmaceutical manner.

It is another object of the present invention to treat certain types of headaches in a manner so as to eliminate the possibility of toxic side effects.

It is still another object of the present invention to treat certain types of headaches in a manner so as to eliminate the possibility of adverse reaction

SUMMARY OF THE INVENTION

These and other objects are accomplished by providing a headache relief headband that comprises an annular strip of material having an inwardly presented surface and an outwardly presented surface. A channel means is defined by the inwardly presented surface and the outwardly presented surface and extends longitudinally along at least a portion of the annular strip of material. A plurality of protuberance means are adjustably positioned within the channel means for applying pressure simultaneously to preselected points on the cranium, whereby when the headband is placed around the head of the wearer above the ears, it provides concentrated pressure to selected points of the cranium which are known to alleviate headaches.

BRIEF DESCRIPTION OF THE DRAWINGS

Some of the features and advantages of the invention having been briefly stated, others will appear from the detailed description which follows, when taken in connection with the accompanying drawings, in which—

DETAILED DESCRIPTION OF THE ILLUSTRATED EMBODIMENT

Figure 1:
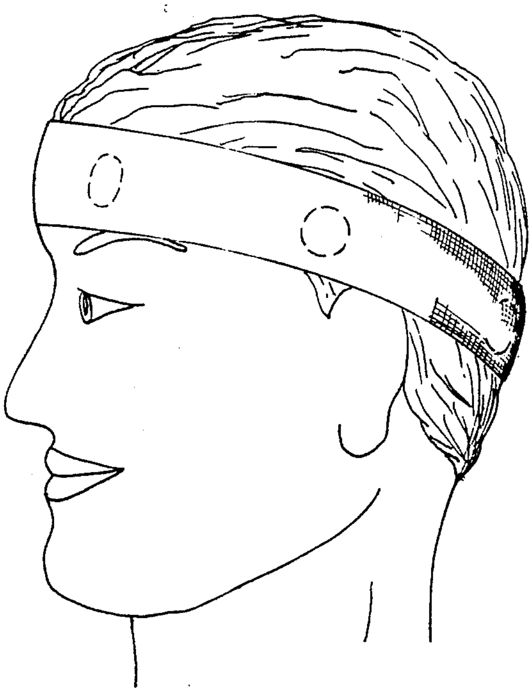
FIG. 1 is a side view of a person wearing the headache relieving headband of the present invention.
Figure 2:
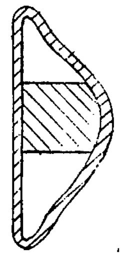
FIG. 2 is a cross sectional view of the headache relieving headband of the present invention taken along line 2—2 of FIG. 3.

While the present invention will be described more fully hereinafter with reference to the accompanying drawings, in which a particular embodiment is shown, it is to be understood at the outset that persons skilled in the art may modify the invention herein described while still achieving the favorable results of this invention. Accordingly, the description which follows is to be understood as a broad teaching disclosure directed to persons of skill in the appropriate arts and not as limiting upon the present invention.

Referring more specifically to the drawings, a headband which embodies the features of the present invention is generally indicated at 10. The headband is adapted to encircle the head of the wearer and to overlie the supraorbital arteries, the temporal arteries and the nuchial ridges on each side of the cranium. The headband comprises an annular strip of material, a channel means and a plurality of protuberances, and a closure means.

The headband 10 comprises an annular strip of material 20 approximately two inches in width having an inwardly presented surface 22 and an outwardly presented surface 24. The headband of the preferred embodiment is fabricated from an elastic woven textile fabric, but may also be made of other types of material such as non-woven textile fabrics as well as synthetic plastic materials and mixtures of the foregoing. In addition, the material need not be elastic, as the required pressure on the cranium may be provided by adjustment of the closure means, as will be described in greater detail hereinbelow.

The annular strip of material includes a channel or channel means 30 defined by the inwardly presented surface 22 and the outwardly presented surface 24 that extends longitudinally along substantially the entire length of the headband 10. It will be noted that the length of the channel may be shortened or that the channel may be divided into a plurality of discrete segments which support a protuberance without sacrificing the efficacy of the headband.

Figure 3:
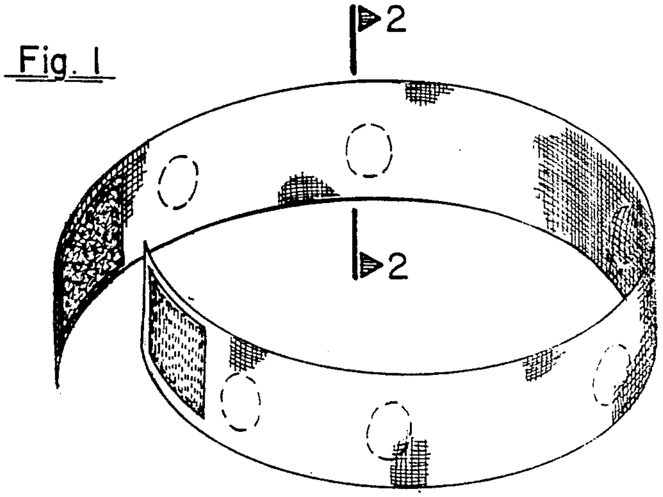
FIG. 3 is a perspective view of the headache relieving headband of the present invention.
Figure 4:
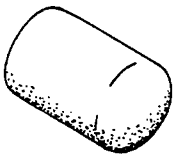
FIG. 4 is a perspective view of a protuberance of the type employed in the present invention.

A plurality of protuberances means or pressure inducers 40 are adjustably positioned within the channel 20 for applying pressure simultaneously to preselected points on the cranium. In the illustrated embodiment, the headband includes six pressure inducers 40 for applying pressure to six preselected points on the cranium. Each pressure inducer has a diameter of approximately $\frac{1}{3}$ the width of the headband, or about $\frac{2}{3}$ of an inch. The pressure inducers 40 are fabricated from a semi-rigid material such as rubber or a synthetic equivalent thereof The headache relieving headband 10 also includes a closure means or closure 50 located at each end of the annular strip of material. As illustrated in FIG. 3, the preferred closure is a two component hook and loop closure such as Velcro ® strip 50*a*, 50*b* is adapted to be detachably connected. Of course, other suitable closures such as snaps, buttons, hooks or loops may be employed with equal efficacy.

In operation, the user first adjusts the position of each of the six pressure inducers within the channel so that they will overlie the desired preselected points on the cranium. Then the band is placed on the cranium of the wearer so that closure means is positioned centrally on the forehead and the pressure inducers contact the preselected points on the cranium. Finally, the tension of the band is adjusted by overlaying the Velcro ® closure means as desired to induce the desired amount of pressure on the cranium. In the illustrated embodiment, the six pressure inducers are adjusted so as to overlie the supraorbital arteries, the temporal arteries, the nuchial ridges. Depending on the type of headache, the wearer may expect a lessening of symptoms within a relatively short period of time after the band is placed in use.

The foregoing embodiments and examples are to be considered illustrative, rather than restrictive of the invention, and those modifications which come within the meaning and range of equivalence of the claims are to be included therein.

That which is claimed is:

1. A headache relieving headband comprising:
- an annular strip of material having an outwardly presented surface and an inwardly presented surface;
- a channel means defined by said inwardly presented surface and said outwardly presented surface extending longitudinally along at least a portion of said annular strip of material;
- a plurality of resilient protuberance means adjustably positioned within said channel means adapted to apply pressure simultaneously to preselected points on the cranium, whereby when the headband is placed around the head of a wearer above the ears, it provides concentrated pressure to selected points of the cranium which are known to contribute to alleviating headaches.

2. A headache relieving headband according to claim 1 wherein said annular strip is chosen from the group of woven textile fabric, non-woven textile fabric, synthetic plastics and mixtures thereof.

3. The headache relieving headband according to claim 2 wherein said annular strip is elastic.

4. The headache relieving headband according to claim 1 wherein said annular strip includes a closure means for closing said annular strip and for providing a means for adjusting the pressure of the protuberances on the cranium to optimize headache relief.

5. The headache relieving headband according to claim 4 wherein said closure means is selected, from the group consisting of snaps, hooks, buttons, loops and hook and loop fasteners.

6. The headache relieving headband according to claim 1 wherein each of said protuberance means comprises a semi-rigid material.

7. The headache relieving headband according to claim 6 wherein each of said protuberance means is rubber.

8. The headache relieving headband according to claim 6 wherein said protuberance means have a diameter of approximately one third the width of said headband.

9. A headache relieving headband comprising:
- an annular strip of material having an outwardly presented surface and a inwardly presented surface adapted to be positioned in contacting relation with the cranium of a wearer;
- a channel defined by said inwardly presented surface and said outwardly presented surface extending longitudinally along substantially the entire length of said strip;
- six resilient pressure inducers adjustably positionable within said channel for applying pressure to six preselected points on the cranium, whereby when the headband is stretched around the head of the wearer above the ears, it provides concentrated pressure to six preselected points of the head which are known to contribute to alleviating headaches.

10. The headache relieving headband according to claim 9 wherein said pressure inducers are adapted to overlie and to apply pressure to the supraorbital arteries, the temporal arteries and the nuchial ridges on each side of the cranium.

11. The headache relieving headband according to claim 10 wherein said pressure inducers comprise a semi-rigid material.

12. The headache relieving headband according to claim 11 wherein said semi-rigid material is rubber.

13. The headache relieving headband according to claim 9 wherein said annular strip includes a closure means for closing said annular strip and for providing a means for adjusting the pressure of the pressure inducers in the cranium for maximum headache relief.

14. The headache relieving headband according to claim 4 wherein said closure means is selected from the group consisting of snaps, hooks, buttons, loops and hook and loop fasteners.

15. A method of treating headaches using a headband of the type adapted to be worn on the cranium of a patient having an annular strip of material having an outwardly presented surface and an inwardly presented surface, a channel defined by the inwardly presented surface and the outwardly presented surface extending longitudinally along the annular strip of material, and a plurality of resilient pressure inducers adjustably positionable within the channel for applying pressure simultaneously to preselected points on the cranium, and a closure for closing the strip and for adjusting the pressure of the protuberances on the cranium comprising the steps of:
- adjusting the position of pressure inducers within the channel so that they overlie preselected points on the cranium;
- placing the annular strip on the cranium of the wearer so that the pressure inducers contact the preselected points on the cranium;
- adjusting the tension on the annular strip so that the pressure on the cranium optimizes headache relief.

* * * * *